United States Patent [19]
> Flynn

[11] 4,303,666
[45] Dec. 1, 1981

[54] 5-PHENYLSELENO-2-BENZIMIDAZOLE CARBAMATES

[75] Inventor: Anthony P. Flynn, Great Budworth, England

[73] Assignee: Imperial Chemical Industries Limited, London, England

[21] Appl. No.: 194,932

[22] Filed: Oct. 7, 1980

[30] Foreign Application Priority Data

Oct. 12, 1979 [GB] United Kingdom ............... 35502/79

[51] Int. Cl.$^3$ ................. A61K 31/415; C07D 235/32
[52] U.S. Cl. ................. 424/273 B; 548/306; 564/441; 564/305
[58] Field of Search ............ 548/306; 424/273 B

[56] References Cited

U.S. PATENT DOCUMENTS

| | | | |
|---|---|---|---|
| 3,929,821 | 12/1975 | Beard et al. | 548/306 |
| 3,929,824 | 12/1976 | Beard et al. | 548/306 |
| 3,965,113 | 6/1976 | Beard et al. | 548/306 |

OTHER PUBLICATIONS

Klayman and Güntner, "Organic Selenium Compounds: Their Chemistry and Biology", (Wiley-Interscience), 1973, pp. 727–761.
E. de Barry Barnett & C. L. Wilson, "Inorganic Chemistry", (Longmans Green & Co.), 1953, p. 5.
Burger, "Medicinal Chemistry", Part II, Fourth Edition, Manfred Wolff, Editors (Wiley), Jan. 1979, pp. 517–518.

*Primary Examiner*—Robert T. Bond
*Attorney, Agent, or Firm*—Cushman, Darby & Cushman

[57] ABSTRACT

The invention relates to novel 5-phenylseleno-2-benzimidazolecarbamate derivatives, for example methyl 5-phenylseleno-2-benzimidazole-carbamate, which possess useful anthelmintic and/or fasciolicidal activity, and processes for the manufacture of the novel compounds, and dosage formulations, are also described.

9 Claims, No Drawings

5-PHENYLSELENO-2-BENZIMIDAZOLE CARBAMATES

This invention relates to novel benzimidazole derivatives, and in particular it relates to novel 5-phenylselenobenzimidazole derivatives which possess anthelmintic and/or fasciolicidal activity.

According to the invention there is provided a 5-phenylselenobenzimidazole derivative of the formula:

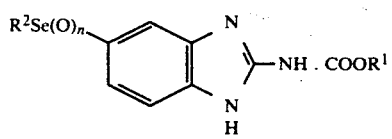

wherein $R^1$ is a 1-6C alkyl radical, $R^2$ is a phenyl radical optionally bearing one or more halogen, cyano, trifluoromethyl or 1-6C alkyl or alkoxy substituents, and n is 0, 1 or 2.

A suitable value for $R^1$, or for a 1-6C alkyl substituent in $R^2$, is, for example, a methyl, ethyl, propyl, butyl, pentyl or hexyl radical, particularly a methyl or ethyl radical and especially a methyl radical; and a suitable 1-6C alkoxy substituent in $R^2$ is, for example, a methoxy, ethoxy, propoxy, butoxy, pentyloxy or hexyloxy radical, particularly a methoxy or ethoxy radical and especially a methoxy radical.

A suitable halogen substituent in $R^2$ is, for example, a chlorine, bromine, fluorine or iodine atom.

n is preferably 0 or 1, particularly 0.

A preferred group of 5-phenylselenobenzimidazole derivatives of the invention comprises compounds of the formula I wherein $R^1$ is a methyl or ethyl radical, $R^2$ is a phenyl or methoxyphenyl radical, and n is 0 or 1, and especially preferred is such a group wherein n is 0.

Particular preferred compounds of the formula I are methyl 5-phenylseleno-2-benzimidazolecarbamate and methyl 5-p-methoxyphenylseleno-2-benzimidazolecarbamate.

The compound of the formula I may be prepared by methods known in themselves for the manufacture of chemically analogous compounds. Thus, according to a further feature of the invention, there is provided a process for the manufacture of a 5-phenylseleno-benzimidazole derivative of the formula I which comprises reacting a diamine of the formula:

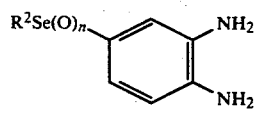

wherein $R^2$ has the meaning stated above, with cyanamide or a 2-(1-6C alkyl)isothiourea and a 1-6C alkyl chloroformate or di(1-6C alkyl)carbonate; or with a mono- or bis-adduct of cyanamide or a 2-(1-6C alkyl)isothiourea and a 1-6C alkyl chloroformate; or with a 1-6C alkyl dichloromethylenecarbamate ($CCl_2$:$N.COOR^1$, wherein $R^1$ is a 1-6C alkyl radical); whereafter, when a compound of the formula I wherein n is 1 or 2 is required, a product of the formula I of a lower oxidation level is oxidised, for example with a peroxycarboxylic acid such as 3-chloroperbenzoic acid.

Diamines of the formula II which are used as starting materials in the above process may be prepared from known intermediates by conventional synthetic reactions which are well-known in the art of organic chemistry. The following description of the preparation of diamine II is by way of example only:

5-Chloro-2-nitroaniline (III) is reacted with a diphenyldiselenide derivative ($R^2Se)_2$, to give a 5-phenylseleno-2-nitroaniline derivative IV, and the derivative IV is reduced with stannous chloride to a required diamine II in which n is 0.

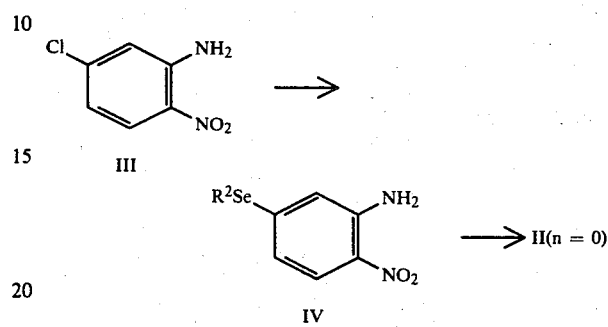

As stated above, the benzimidazole derivatives of the formula I possess anthelmintic activity, and they possess such activity against both the adult and larval stages. For example, in sheep carrying a natural mixed helminth infection, a dose of 5 mg. per kg. of methyl 5-phenylseleno-2-benzimidazolecarbamate effectively removed all adult and immature worms, as assessed by post-mortem examination seven days later. The compound itself produced no apparent toxic effect in the sheep.

When they are used to combat helminth or Fasciola infestations in domestic animals, for example sheep, cattle, goats or horses, the benzimidazole derivatives of the formula I are preferably administered orally in the form of a drench, such that each animal receives a dose of from 1 to 100 mg. per kg., and the animals are dosed at intervals of 2 to 3 weeks during the period when there is the greatest risk of infestation.

The benzimidazole derivatives of the formula I are used in the form of conventional anthelmintic or fasciolicidal compositions comprising an anthelmintically- or fasciolicidally-effective amount of the 5-phenylselenobenzimidazole derivative of the formula I together with a pharmaceutically or veterinarily acceptable diluent or carrier, and such a composition is provided as a further feature of this invention.

Such a composition may conveniently be in the form of a drench, bolus, salt-lick or in-feed formulation, and may be manufactured by conventional techniques using conventional excipients. A preferred formulation is a drench containing from 4 to 50 g. per liter of methyl 5-phenylseleno-2-benzimidazolecarbamate.

The invention is illustrated but not limited by the following Examples:

Example 1

A mixture of 1,2-diamino-4-phenylselenobenzene (11.3 g. 43 mmole) and 1,3-bis(methoxycarbonyl)-2-methylisothiourea (10.3 g., 50 mmole) in glacial acetic acid (10 ml.), ethanol (100 ml.) and water (100 ml.) was boiled under reflux for two hours and allowed to cool. The reaction mixture was filtered, and the solid product was crystallised from a mixture of equal volumes of acetic acid and methanol to give methyl 5-phenylseleno-2-benzimidazolecarbamate, m.p. 238°-240° C.

The 1,2-diamino-4-phenylselenobenzene used as the starting material in the above process may be prepared as follows:

Diphenyldiselenide (6.2 g.) was stirred in ethanol (50 ml.) under an atmosphere of nitrogen, and sodium borohydride (1.6 g.) was added, followed by a solution of 5-chloro-2-nitroaniline (6.5 g.) in tetrahydrofuran (50 ml.). The mixture was stirred, and boiled under reflux under nitrogen for 10 hours, then was cooled, poured into water (200 ml.) and filtered. The solid product was crystallised from ethanol, to give 5-phenylseleno-2-nitroaniline, m.p. 126° C.

A solution of stannous chloride dihydrate (50 g.) in concentrated hydrochloric acid (100 ml.) was stirred and heated at 60°–70° C. while 5-phenylseleno-2-nitroaniline (14.6 g.) was added in portions. The mixture was stirred at that temperature for 2 hours, and was then cooled and filtered. The solid product was stirred with concentrated sodium hydroxide solution and extracted with ether. The ether extract was separated and dried, and the solvent was evaporated to give the required starting material, 1,2-diamino-4-phenylselenobenzene as a yellow oil which slowly crystallised.

Example 2

A solution of methyl 5-phenylseleno-2-benzimidazolecarbamate (5.0 g, 14.5 mmole) in acetic acid (50 ml.) was cooled to 10°–15° C. while 85% 3-chloroperbenzoic acid (3.0 g, 14.7 mmole) was added in portions. The solution was then allowed to warm to room temperature, and the solvent was evaporated under reduced pressure. The residue was stirred with sodium carbonate solution and filtered, and the solid product was crystallised from a mixture of equal parts of acetic acid and methanol, to give methyl 5-phenylseleninyl-2-benzimidazolecarbamate, m.p. 222° C. with decomposition. All other 5-phenylseleninylbenzimidazole carbamates of the invention may be manufactured in exactly the same manner, by using the appropriate 1-6C alkyl 5-(optionally substituted phenyl)-seleno-2-benzimidazolecarbamate in place of methyl 5-phenylseleno-2-benzimidazolecarbamate.

Example 3

The process described in Example 1 was repeated, using 1,2-diamino-4-p-methoxyphenylselenobenzene as the starting diamine, to give methyl 5-p-methoxyphenylseleno-2-benzimidazolecarbamate, m.p. 230°–232° C.

The diamine starting material was prepared from 5-p-methoxyphenylseleno-2-nitroaniline, m.p. 120°–122° C., by the process described in the last paragraph of Example 1, and was isolated as the dihydrochloride, m.p. 162°–163° C.

All other 5-phenylselenobenzimidazole carbamates of the invention may be manufactured in exactly the same way, by using the appropriate 1,2-diamino-4-(optionally substituted phenyl)selenobenzene in place of 1,2-diamino-4-phenylselenobenzene, and the appropriate 1,3-bis(1-6C alkoxycarbonyl)-2-methylisothiourea in place of 1,3-bis(methoxycarbonyl)-2-methylisothiourea.

What we claim is:

1. A compound of the formula:

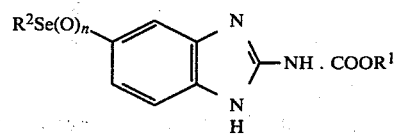

wherein $R^1$ is 1–6C alkyl, $R^2$ is phenyl optionally bearing one or more halogen, cyano, trifluoromethyl or 1–6C alkyl or 1–6C alkoxy substituents, and n is 0, 1 or 2.

2. A compound as claimed in claim 1 wherein $R^1$ is a methyl, ethyl, propyl, butyl, pentyl or hexyl, and $R^2$ is phenyl optionally bearing one or more chlorine, bromine, fluorine or iodine atoms, or cyano, trifluoromethyl, methyl, ethyl, propyl, butyl, pentyl, hexyl, methoxy, ethoxy, propoxy, butoxy, pentyloxy or hexyloxy as substituents.

3. A compound as claimed in claim 2 wherein n is 0.

4. A compound as claimed in claim 1 wherein $R^1$ is methyl or ethyl, $R^2$ is phenyl or methoxyphenyl and n is 0 or 1.

5. A compound as claimed in claim 4 wherein n is 0.

6. A compound as claimed in claim 1 which is methyl 5-phenylseleno-2-benzimidazolecarbamate.

7. A compound as claimed in claim 1 which is methyl 5-p-methoxyphenylseleno-2-benzimidazolecarbamate.

8. An anthelmintic or fasciolicidal composition comprising an anthelmintically- or fasciolicidally-effective amount of a compound as claimed in claim 1 together with a pharmaceutically or veterinarily acceptable diluent or carrier.

9. A method of combatting helminth or Fasciola infestations in domestic animals which comprises administering to such animals exposed to such infestations an anthelmintically or fasciolicidally effective amount of a compound as claimed in claim 1.

* * * * *